Jan. 15, 1952 W. S. HAHN Plant Pat. 1,067
IVY PLANT
Filed July 11, 1950
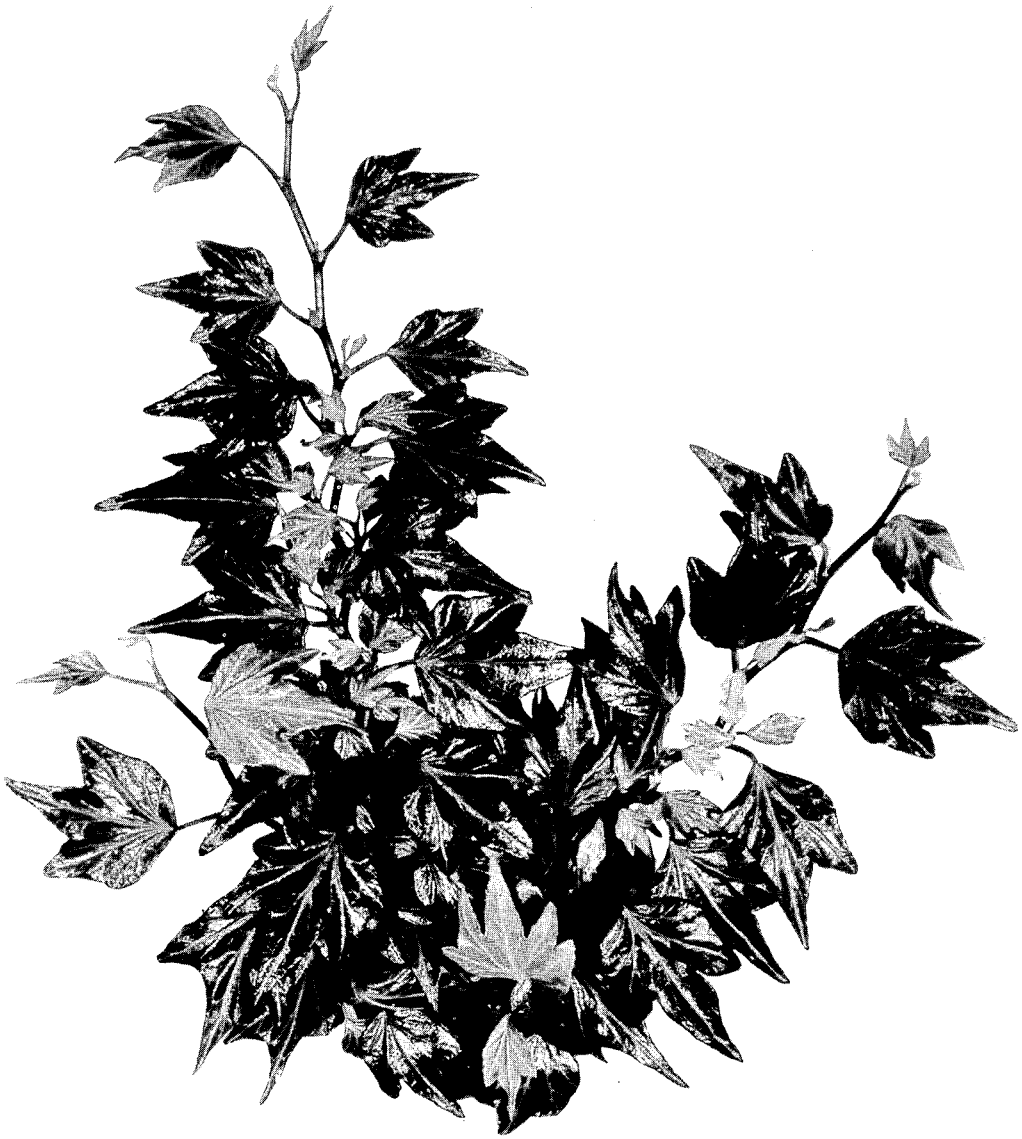
INVENTOR
Walter S. Hahn
By Orville M. Kile
Plant Pat. Agt.

Patented Jan. 15, 1952

Plant Pat. 1,067

UNITED STATES PATENT OFFICE 1,067

IVY PLANT

Walter S. Hahn, Pittsburgh, Pa., assignor to Louis Hahn & Son, Pittsburgh, Pa.

Application July 11, 1950, Serial No. 173,138

1 Claim. (Cl. 47—59)

This new variety (*Hedera helix*) was discovered by me as a sport or mutation of Hahn's Maple Queen Ivy (Plant Patent No. 429) in my extensive greenhouses in the suburbs of Pittsburgh where I constantly search for new and promising varieties. It has been reproduced by me by means of cuttings for several years at my greenhouses. It is a hardy and vigorous grower and thrives readily in open fields in that latitude.

The accompanying illustration shows a potted plant of this variety at the age of about four months, under average growing conditions.

Like our other self-branching varieties, this new variety of ivy makes a compact and rapid growth. After growing to an upright height of three to four inches it begins to recline and if suspended assumes a graceful pendulous form with long branches. However this variety will climb when planted against stone, brick or wood. In the plants of the age shown in the illustration, these climbing attachments are almost completely absent.

This variety differs from other self-branching, pendulous varieties chiefly in the shape, veination and general appearance of the leaves as well as in the manner in which the leaves arrange themselves on the stems. The leaves on the separate branches do not overlap as much or produce as dense growth as most other varieties of this class, mainly because the individual leaves are smaller, although there are varieties having even smaller leaves. While the petioles of the leaves are not short as compared with some of my varieties, the self-branching habit marked in this variety by the tendency to produce many small leaves near the main stems, has the effect of filling in a pleasing way what would otherwise be open space between the leaves near the main stems of the newer branches.

The internodes are of medium length and at each node the stem makes a decided angle instead of growing in one straight line, thus giving the stem a zig-zagged form. The petioles rise at a sharp angle from the stem.

The mature leaves are five-lobed, but the lower two lobes may be somewhat indistinct, especially on young leaves. The central or terminal lobe is lanceolate in form and inclined to curve downward gracefully at the tip. The tips of the other two prominent lobes are notably sharp pointed.

The size of the individual leaf varies with age and the conditions of growth but would be called medium to small, ranging from one to two inches in width at the widest point and being one-third to one-half longer than wide. The petioles of the third to fifth leaves from the end of a growing branch will measure approximately three-fourths of an inch in length. This length increases with the distance from the end of a branch; that is, as the leaves and branches mature. The leaves would not, however, be described as "narrow" or "dainty" or as giving the plant a "lacy" appearance as is true of certain other varieties.

The veination of the leaves is prominently raised (varix) and causes a more ventricose effect than in most other varieties. The veins are also a lighter green than the leaf blade and the contrasting effect is further heightened by the reflected lights from the raised veins. At the point where the edges of the long lanceolate lobe meets the edges of the other lobes the downward curving of the lobes causes an upfolding or wrinkling, as of excess material. All this gives the branch and plant a trachyplueral and repandent effect suggesting crepe de Chine in appearance, and an effect quite different from the usual flat appearance of other varieties.

Color of the leaves and stems is not a distinctive feature of this variety, the leaves being the usual dark green on the upper surface and a lighter green on the lower surface, with the main stems showing slight touches of brown.

Having thus disclosed my discovery, I claim:

The new and distinct variety of ivy plant of the self-branching type, characterized particularly by its medium to small leaves having a distinctive shape and veination, repandent surface, and borne on petioles of medium length which attach to the zig-zagged stem at a sharp angle, as described and illustrated, thereby producing a novel appearance described as suggesting crepe de Chine.

WALTER S. HAHN.

No references cited.